United States Patent
Hakki et al.

(10) Patent No.: US 9,775,991 B1
(45) Date of Patent: *Oct. 3, 2017

(54) ENDOVASCULAR ELECTRODE SYSTEM FOR TISSUE STIMULATION WITH EMBEDDED GENERATOR

(71) Applicants: A-Hamid Hakki, Dunedin, FL (US); A-Hadi Hakki, Largo, FL (US)

(72) Inventors: A-Hamid Hakki, Dunedin, FL (US); A-Hadi Hakki, Largo, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 15/042,301

(22) Filed: Feb. 12, 2016

Related U.S. Application Data

(63) Continuation-in-part of application No. 13/649,792, filed on Oct. 11, 2012, now Pat. No. 9,289,593.

(60) Provisional application No. 61/545,913, filed on Oct. 11, 2011.

(51) Int. Cl.
 *A61N 1/05* (2006.01)
 *A61N 1/362* (2006.01)
 *A61N 7/00* (2006.01)

(52) U.S. Cl.
 CPC ............ *A61N 1/057* (2013.01); *A61N 1/362* (2013.01); *A61N 7/00* (2013.01)

(58) Field of Classification Search
 CPC ....... A61N 1/3756; A61N 1/362; A61N 1/057
 USPC ................................................. 607/115, 116
 See application file for complete search history.

(56) References Cited

U.S. PATENT DOCUMENTS

| | | | |
|---|---|---|---|
| 5,224,491 A | 7/1993 | Mehra | |
| 5,282,845 A | 2/1994 | Bush et al. | |
| 5,383,922 A | 1/1995 | Zipes et al. | |
| 5,749,833 A | 5/1998 | Hakki et al. | |
| 5,814,089 A | 9/1998 | Stokes et al. | |
| 5,902,331 A | 5/1999 | Bonner et al. | |
| 6,148,237 A | 11/2000 | Das | |
| 6,161,029 A | 12/2000 | Spreigl et al. | |
| 6,185,464 B1 | 2/2001 | Bonner et al. | |
| 6,219,581 B1 | 4/2001 | Schaldach et al. | |
| 6,256,543 B1 | 7/2001 | Spence | |
| 6,345,198 B1 | 2/2002 | Mouchawar et al. | |
| 6,370,427 B1 | 4/2002 | Alt et al. | |
| 6,400,992 B1 | 6/2002 | Borgersen et al. | |
| 6,434,430 B2 | 8/2002 | Borgersen et al. | |

(Continued)

FOREIGN PATENT DOCUMENTS

| | | | |
|---|---|---|---|
| WO | 9713941 A1 | 4/1997 | |
| WO | 9832485 A1 | 7/1998 | |

(Continued)

OTHER PUBLICATIONS

K.L. Lee, et al., First Human Demonstration of Cardiac Stimulation with Transcutaneous Ultrasound Energy Delivery: Implications for Wireless Pacing with Implantable Devices. J Am Coll Cardiol. 2007;50:877-83.

(Continued)

*Primary Examiner* — Alyssa M Alter
(74) *Attorney, Agent, or Firm* — Rosenberg, Klein & Lee

(57) ABSTRACT

A system to generate and sense electrical energy to and from tissue within a mammalian body. The system includes a flexible shaft and an electrical generator disposed on or embedded within the flexible shaft. Radially displaceable arcuate arm members forming electrodes are displaceable responsive to actuation of the electrical generator.

19 Claims, 7 Drawing Sheets

(56) References Cited

U.S. PATENT DOCUMENTS

| | | |
|---|---|---|
| 6,445,953 B1 | 9/2002 | Bulkes et al. |
| 6,505,081 B1 | 1/2003 | Das |
| 6,522,915 B1 | 2/2003 | Ceballos et al. |
| 6,529,777 B1 | 3/2003 | Holmstrom et al. |
| 6,544,270 B1 | 4/2003 | Zhang |
| 6,574,512 B1 | 6/2003 | Zhang et al. |
| 6,584,352 B2 | 6/2003 | Combs et al. |
| 6,654,638 B1 | 11/2003 | Sweeney |
| 6,654,644 B2 | 11/2003 | Sanchez-Zambrano |
| 6,658,289 B2 | 12/2003 | Helland |
| 6,671,562 B2 | 12/2003 | Osypka et al. |
| 6,675,045 B2 | 1/2004 | Mass et al. |
| 6,721,600 B2 | 4/2004 | Jorgenson et al. |
| 6,772,015 B2 | 8/2004 | Dahl et al. |
| 6,788,972 B2 | 9/2004 | Prutchi et al. |
| 6,795,732 B2 | 9/2004 | Stadler et al. |
| 6,856,835 B2 | 2/2005 | Bardy et al. |
| 6,868,291 B1 | 3/2005 | Bonner et al. |
| 6,871,101 B2 | 3/2005 | Zhang et al. |
| 6,885,889 B2 | 4/2005 | Chinchoy |
| 6,936,040 B2 | 8/2005 | Kramm et al. |
| 6,968,236 B2 | 11/2005 | Hagele |
| 6,973,351 B2 | 12/2005 | Morgan |
| 6,980,850 B1 | 12/2005 | Kroll et al. |
| 6,985,777 B2 | 1/2006 | Tsuboi et al. |
| 6,988,001 B2 | 1/2006 | Greatbatch et al. |
| 6,993,379 B1 | 1/2006 | Kroll et al. |
| 7,031,774 B1 | 4/2006 | Doan et al. |
| 7,047,086 B2 | 5/2006 | Taskiran et al. |
| 7,092,766 B1 | 8/2006 | Salys et al. |
| 8,923,963 B2 | 12/2014 | Bonner et al. |
| 9,072,914 B2 | 7/2015 | Greenhut et al. |
| 9,216,280 B1 * | 12/2015 | Hakki .................... A61N 1/05 |
| 9,289,593 B1 * | 3/2016 | Hakki .................... A61N 1/05 |
| 2002/0035381 A1 | 3/2002 | Bardy et al. |
| 2002/0193836 A1 | 12/2002 | Schmidt |
| 2003/0092977 A1 * | 5/2003 | Sahatjian ........... A61B 5/02007 |
| | | 600/381 |
| 2004/0176672 A1 | 9/2004 | Silver et al. |
| 2008/0255642 A1 | 10/2008 | Zarins et al. |

FOREIGN PATENT DOCUMENTS

| | | |
|---|---|---|
| WO | 0004950 A2 | 2/2000 |
| WO | 02087501 A2 | 11/2002 |
| WO | 2004045675 A2 | 6/2004 |
| WO | 2006083617 A2 | 8/2006 |

OTHER PUBLICATIONS

D. Reynolds, et al., A Leadless Intracardiac Transcatheter Pacing System, The New England Journal of Medicine, Nov. 10, 2015.

M. Schoenfeld, Contemporary Pacemaker and Defibrillator Device Therapy: Challenges Confronting the General Cardiologist. J. Am. Heart Association. 2007; 115:638-53.

* cited by examiner

ENDOVASCULAR ELECTRODE SYSTEM FOR TISSUE STIMULATION WITH EMBEDDED GENERATOR

REFERENCE TO RELATED APPLICATIONS

This application is a Continuation-in-Part of application Ser. No. 13/649,792, filed on 11 Oct. 2012, now U.S. Pat. No. 9,289,593, which Application was based on Provisional Patent Application Ser. No. 61/545,913 filed on 11 Oct. 2011.

INCORPORATION BY REFERENCE

Application Ser. No. 13/649,792 and 61/545,913 are hereby incorporated by reference.

FIELD OF THE INVENTION

The invention relates to the field of cardiology and in particular to systems for pacemaker implantation. More in particular, this invention is directed to the field of treatment of symptomatic bradycardia through cardiac pacing using surgically inserted subcutaneous generators in conjunction with transvenous leads providing the electrical pacing to the cardiac conduction system. Still further, the present system relates to the field of pacemaker leadless systems for providing pacing of the tissue by an intravascular self-retaining electrode system, and an embedded generator which is able to detect and induce electrical and mechanical cardiac action.

The subject system is in the area of sensing myocardial electrical impulses, as well as providing low/high voltage pacing and defibrillation. The subject system is further directed to the field of permitting pacing using electric, ultrasound, or magnetic stimulation permitting wireless stimulation of the tissue.

The subject system concept is further directed to the field of providing simultaneous pacing of right and left cardiac chambers by way of intravascular electrodes for treating heart failure and provides for a homogeneous electric field for defibrillation.

BACKGROUND OF THE INVENTION

Conventional cardiac pacemakers and defibrillators generally consist of a generator for electrical stimulation and an elongated flexible pacemaker lead that is connected proximally to a header structure on the generator which is implanted distally from the heart for cardiac pacing and defibrillation. The cardiac lead is generally configured with tubular electrically insulated sleeve structures that are inserted into the body through an incision overlying veins leading to the heart chambers where the distal end of the lead is lodged. In such cases, the distal end of the lead is connected to a tubular tip electrode, having an increased diameter forming an annular shoulder against which the distal end of the sleeve abuts.

Biocompatible silicone based adhesives are generally used to connect the distal end of the lead sleeve and the tip electrode. Among the limitations of adhesives is that the manufacture of the assembled lead requires sufficient time for the adhesive to cure, and the adhesive's bond strength may decrease in time and permit separation from the tip electrode from the sleeve. Fixing the distal end of the lead to cardiac tissue is accomplished generally by conventional anchoring systems. One such active fixation mechanism involves a screw-in electrode and further there has been used a passive fixation mechanism consisting of one or more radial tines that engage the inner lining of the heart or blood vessel.

Such conventional devices are typically employed and include a single chamber device as well as a dual chamber device. The single chamber device is capable of sensing and pacing in one chamber, either in the atrium or in the ventricle. Dual chamber devices have the capability of sensing and pacing in both chambers. Modes of pacing include VDD, DVI, VVI, and DDD, where the first letter of the mode indicates the chamber being paced, with the second letter indicating the chamber being sensed, and the third letter indicating inhibited or triggered responses. A fourth letter "R" may denote rate responsive pacing to match a patient's activities. In addition to pacing the right/atrium and ventricle pacing, the left ventricle by way of the cardiac veins or biventricular pacing provides a physiologic and synchronous cardiac contraction which would improve cardiac function.

There are basically two types of leads which are uni-polar and bipolar leads. The uni-polar lead has a single conductor coil with typically a cathode, or negative pole, at the distal tip and an anode, or positive pole, defined by the housing of the stimulator. Electric current returns to the anode via body tissue as a current path. In opposition, a bipolar lead has two conductor coils, the distal tip forming the cathode and an annular or ring electrode located a few millimeters proximal to the distal tip. High voltage defibrillation is delivered by the one or two shocking coils which are inserted intravenously.

Pacemaker leads which have been used are generally suited for placement in the ventricle and atrium. In order to provide permanent pacing and to avoid pacemaker lead dislodgement, various methods have been used for anchoring the leads to the endocardium which is the inner lining of the heart chambers. Conventional right ventricular apical pacing alters the normal synchronization of different heart chambers, and may adversely influence ventricular function, leading to heart failure, and increased mortality.

Biventricular pacing or resynchronization requires the placement of electrodes within the venous system of the heart. However, other than lodging the tip of the lead into the distal coronary vein, there has been found no safe anchoring mechanism to maintain the lead from dislodging. Additionally, the optimum lodging site may not be the ideal pacing location for effective myocardial stimulation. Screw-in anchors may be applied to the myocardium, but cannot be utilized in vascular structures due to the risk of endothelial damage and hemorrhage.

Conventional pacemaker right ventricular leads have the disadvantage that they must cross the tricuspid valve. Such leads may cause unwanted tricuspid regurgitation by interfering with tricuspid valve closing in heart contraction which may interfere with the right ventricular function.

PRIOR ART

It is known in the prior art to provide systems for treatment of symptomatic bradycardia through cardiac pacing using surgically inserted subcutaneous generators in conjunction with one or more transvenous leads that provide electrical pacing to the cardiac conduction system. However, it has been found that complications arise in a certain percentage of patients with many of these directly related to the electrical generator or the transvenous lead wire system and include problems associated with infection, pocket hematoma, pneumothorax, lead fracture, dislodgement and vascular access limitations.

Single chamber ventricular systems are generally limited to patients with atrial fibrillation and slow ventricular response where the patient does not require frequent pacing. Frequent ventricular apical pacing has been shown to be deleterious to cardiac function. There are numerous conditions which would preclude the implantation of a transvenous pacemaker system, such as compromised venous access, the need to preserve veins for hemodialysis, thrombosis, a patient's history of infection, or the need for an indwelling venous catheter.

Prior art leadless pacemakers include limitations wherein the devices require an anchoring system in the form of screws or tines. In particular, the Nanostim device (St. Jude Medical) uses a helical wire screw, while the Micra system (Medtronic) uses tines and are delivered to the right ventricle by way of the femoral vein and such has a reattachable mechanism for extraction. Such devices solely pace the ventricle and thus do not permit atrioventricular synchrony. In particular, the prior art Micra transcatheter pacemaker (Medtronic) is a single-chamber ventricular pacemaker which is self-contained in a hermetically enclosed capsule. The implantation procedure for the transcathether pacemaker uses a steerable catheter delivery system and is inserted through a femoral vein by use of a 23-French introducer. Such leadless prior art devices do not supplant traditional lead-containing transvenous pacemakers. Such devices are generally used only for single-chamber ventricular pacing. This procedure is generally reserved for patients with atrial fibrillation and bradycardia or for use in patients who only need infrequent pacing. Such prior art systems are not useful in the treatment of the majority of pacemaker recipients that include patients with sinus-node dysfunction or heart block and do not have a role in the treatment of patients with heart failure who need left-ventricular resynchronization for improvement of cardiac output. (Dr. Mark S. Link; New England Journal of Medicine Nov. 9, 2015). In contrast, the subject system has distinctive features compared to prior art leadless pacemaker devices.

Other leadless pacemaker devices are shown in U.S. Pat. Nos. 5,814,089; 6,522,915; 6,584,352; 8,923,963; and, 9,072,914. However, such prior art systems are generally not self-retaining and require fixation tines or helical fixation when inserted into a patient's body. Such prior art systems generally do not provide for an adjustable diameter size and have limited endothelial contact.

Such prior art devices generally do not provide for contiguous atrial and ventricular pacing and do not present a low profile design and further do not have a variable electrode orientation capability, see Table 1.

TABLE 1

Features of Leadless Pacemaker Devices (LPD)

| Features | LPD* | Current Patent |
|---|---|---|
| Battery within device | Yes | Yes |
| Leadless | Yes | No |
| Adjustable device diameter | No | Yes |
| Helical fixation/Tines | Yes | No |
| Contiguous A and V pacing# | No | Yes |
| Ideal for Bi-V pacing | No | Yes |
| Coronary sinus/vein use | No | Yes |
| Low profile design | No | Yes |
| Overlapping electrodes | No | Yes |
| Need for future extraction$ | Yes | No |

TABLE 1-continued

Features of Leadless Pacemaker Devices (LPD)

| Features | LPD* | Current Patent |
|---|---|---|
| Device within device$ | No | Yes |
| Variable electrode orientation | No | Yes |
| Electrode surface area | Small | Large |
| Flexible design | No | Yes |

*Leadless Pacing Device: U.S. Pat. Nos.: 5,814,089; 6,522,915 B1; 6,584,352 B2; 8,923,963 B2; 9,072,914 B2.
A = atrial, V = Ventricular
$= Needed for depleted battery Conventional pacemaker generators permit sensing of electrical cardiac action by use of electrodes embedded in the endocardium or vascular structures of the heart. Without the electrodes, generators are unable to detect electrical or mechanical cardiac action. For a wireless system, it would be desirable for generators to detect and induce electrical and mechanical action. Such prior art conventional generators are generally disk-shaped and may not be suitable for operability in close proximity to cardiac structures. An electrical generator embedded within an electrically conductive shaft coupled in itself to the electrodes would be desirable to conform to the intercostal space which is the space between the ribs of the chest overlying the heart and provide a proximity to cardiac structures for transfer of electrical/ultrasound/Doppler/infrared and magnetic signals.

Kurth and Worley (PCT Publication WO2004/045675) teaches an introducer through which a pacemaker lead is guided. This introducer is formed with a distal end comprising an anchor attached to the walls of the cardiac chambers. Through use of such prior art introducers, there is permitted steering of the pacemaker lead and prevented from displacements or folding onto itself due to the lack of support.

Another prior art system, U.S. Pat. No. 6,654,683, teaches an ultrasonically activated implantable cardiac electrode system, whereby piezoelectric elements convert mechanical energy into electrical energy sufficient to cause pacing of the cardiac tissue. Mechanical energy may originate from an external source low frequency ultrasound transmitter. The electrical energy produced by the piezoelectric element delivers pacing level electrical energy between the system's anode/cathode. Active fixation elements using tines, hooks, and barbs are provided, and such does not teach the use of an embedded generator.

The prior art system does not use the data to send signals to a wireless ring electrode configuration and thus, the ring electrodes do not require a power source, since the generator functions as the sensing system and provides the logic necessary to synchronize the stimulation of tissues. An algorithm is used for determining the timing and sequence of stimulation of cardiac tissues for generators attached to the electrode wires embedded in the cardiac chambers.

U.S. Pat. No. 6,256,543 discloses a temporary pacemaker lead having a pair of connections with releasable engagement so as to permanently affix the electrode to the heart tissue. The electrode may be in the form of a piece of metal, such as a clip, and when the lead wire is removed from the heart, such is released from the electrode and may be reattached.

SUMMARY OF THE INVENTION

An implantable device and system is provided which serves to sense, pace, and shock various cardiac tissues. The subject system employs electrodes which are suitable for vascular structures such as a venous or arterial system which uses leads of different configurations. The leads are collapsible in a pre-deployment configuration and expand for deployment once positioned at the desired location.

The subject implantable system employs electrodes which are suitable for vascular structures with the electrodes collapsible in a pre-deployment configuration and expanded for deployment once located at the desired location. The energy source or electrical generator for the electrodes is contained within a relatively flexible and electrically conductive shaft of the system which is connected to the electrodes and obviates the need for external source of energy or electricity.

Thus, the subject system generates and senses electrical energy to and from tissue within a mammalian body. The system includes an electrically conductive shaft which is insertable within the mammalian body and has a defined shaft axis line. An electrical generator is embedded within the flexible and electrically conductive shaft for producing and sensing electrical energy. An electrically conductive expandable electrode is connected to the electrically conductive shaft. The expandable electrode is radially displaceable with respect to the shaft axis line which defines a longitudinal direction for contiguous contact with a wall of the tissue. The expandable electrode includes a pair of arcuate arm members which extend in a transverse direction with respect to the longitudinal direction from opposing sides of the electrically conductive shaft. Two arcuate arm members have overlapping sections prior to the radial expansion of the electrically conductive expandable electrode with the two arcuate arm members located in a substantially singular plane, each with respect to the other. The two arm members are displaceable responsive to actuation by the electrical generator.

DETAILED DESCRIPTION OF THE PREFERRED EMBODIMENTS

The following description with reference made to the accompanying figures is not to be interpreted in a limited sense. It is to be noted that other embodiments may be utilized without departing from the scope of the current invention, as defined in the Claims appended to this description.

In accordance with the present invention, a pacemaker lead system generally comprises a series of expandable and collapsible ring electrodes. Each ring electrode includes two or more curved electrode portions that may overlap before deployment, and fan out when deployed, in order to conform to the shape of the vascular or cardiac structure at which it is deployed. This facilitates endothelialization of the electrodes by the body fluids and cells.

Figure 1:
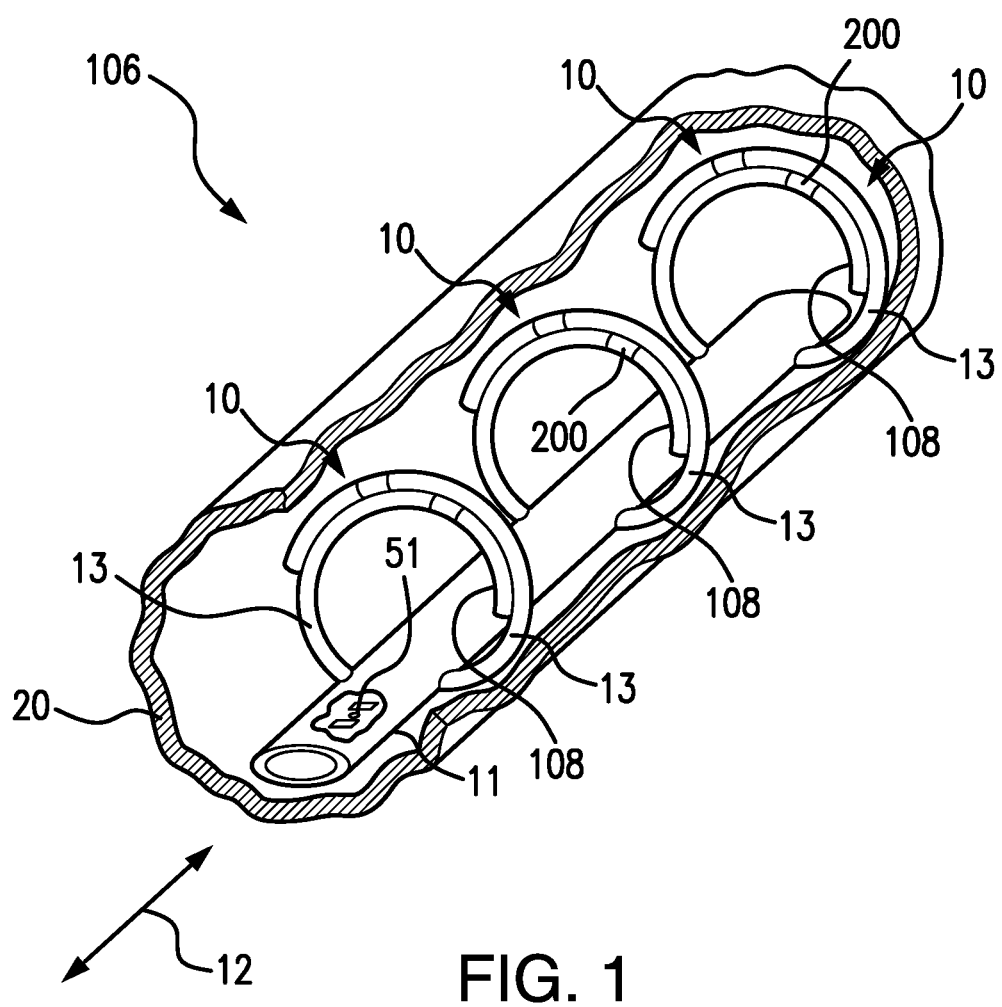
FIG. 1 is a schematic perspective view illustrating the subject system for generating and sensing electrical energy to and from tissue within a mammalian body showing an embedded electrical generator within an electrically conductive shaft in a pre-deployment configuration.

Referring now to FIGS. 1-6, there is shown a system (8) for generating and sensing electrical energy to and from mammalian tissue within a patient body and/or the wall of a mammalian vessel or patient's vessel (20). System 8 includes generator (51) adapted to be received within body (100) of the patient and particularly, in the intercostals region (102) located between patient ribs (104). Additionally, system 8 may include electrical generator 51 embedded within shaft 11 as shown in FIG. 1. Alternatively, electrical generator (65) may be located external the patient's body (100) for wireless transmission of electrical energy as will be discussed in following paragraphs. An important advantage of embedding generator 51 within shaft 11 is that the embedded generator 51 minimizes interference with ultrasonic or electrical signals. Thus, either electrical generator (51) or (65) produce and sense electrical energy passing to and from the wall of a mammalian vessel (20) or tissue within a patient's body.

Of importance is that the system (8) includes lead system (106) which includes the electrically conductive lead or shaft (11) which has embedded therein generator (51) or (65) and is insertable within the vessel (20) or in proximity to mammalian tissue within a patient's body. The lead or shaft (11) includes a lead axis line (12) which may be curvilinear in extent due to the fact that lead or shaft (11) may be inserted into the patient's body in a tortuous contour. Lead system (106) further includes a plurality of expandable electrodes (10) coupled to the lead or shaft (11) on opposing sides thereof. Electrodes 10 and component parts may be formed of suitable compositions such as iridium, platinum, or like composition which provides optimal sensing, pacing or shock. Electrodes (10) are radially displaceable with respect to axis line (12) for providing contiguous contact with the patient's tissue or an inner wall of the vessel (20) when lead system (106) is in the deployed mode of operation. Electrical generators 51 have been fabricated having a dimensional contour adaptable for insertion and containment within lead or shaft 11.

Embedded generator 51 as used in the subject system is embedded in or on shaft 11 has a 0.63 $cm^3$ volume and measures 5.0 cm in length, 0.5 cm in width, and 0.25 cm in height. Generator 51 is easily insertable within the coronary sinus which measures 7.0 cm in length, with a 0.7 cm diameter and has a 2.0 cm circumference. Other commercially available generators include a generator sold by Pacesetter, Inc. under the Trademark Nanostim® as well as Medtronic, Inc. under the Trademark Micra®.

In overall concept, the subject system is adaptable as a pacemaker lead system including a series expandable and collapsible ring electrodes (depicted by the element members 10). Each of the ring electrodes 10 include a pair of arm members 13 which have segments which overlap prior to deployment and then radially expand or fan out when lead system 106 is deployed to conform to the shape of the vascular or cardiac structure to which it is deployed. This facilitates endothelialization of the electrodes by the body fluids and cells as well as providing a larger surface area of contact between the leads and vascular structures.

Figure 2:
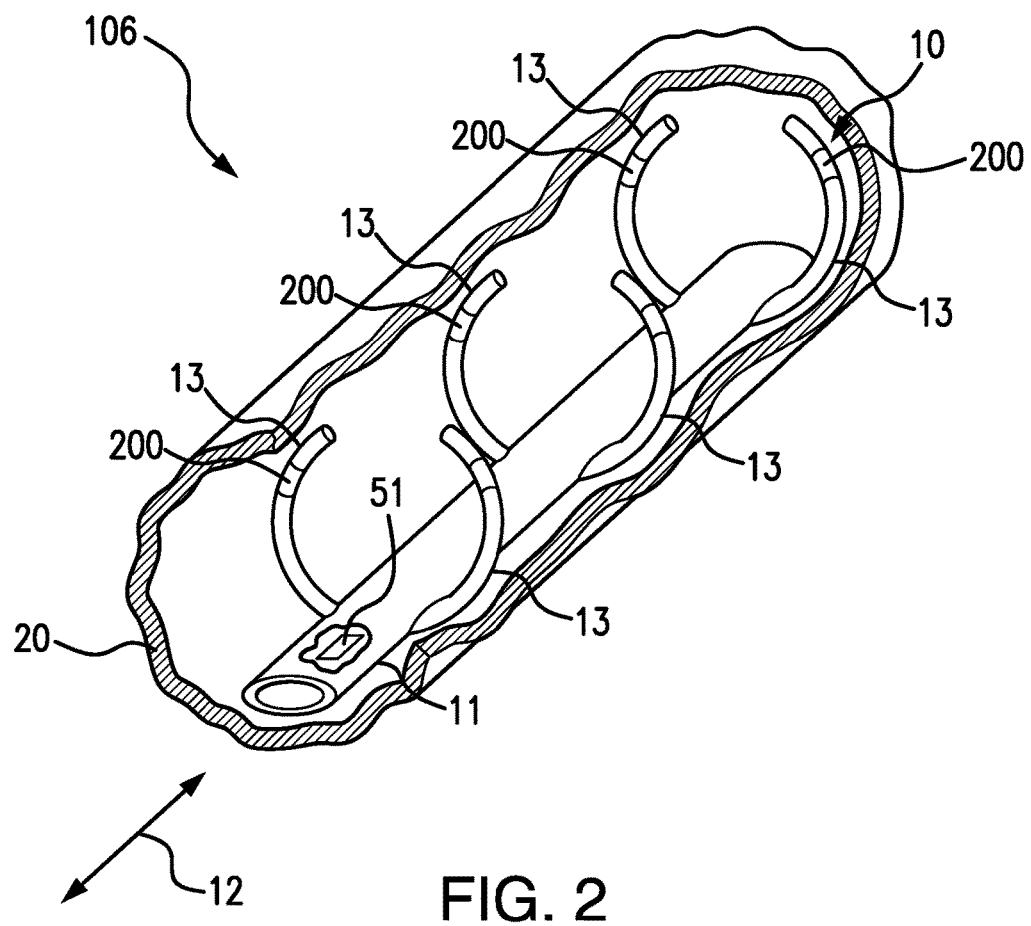
FIG. 2 is a schematic perspective view illustrating the system depicted in FIG. 1 in a deployment configuration.

FIG. 1 depicts lead system (106) in the pre-deployment stage where electrodes (10) are shown in overlapping relation to minimize the cross-sectional area for insertion into the vessel (20). FIG. 2 shows the pacemaker lead system (106) in a deployed position subsequent to expandable electrodes (10) being radially expanded. As FIG. 2 illustrates, in its deployed position, the radially expanded electrodes (10) contiguously contact an inner wall of vessel (20).

Each of electrodes (10) has a pair of arm members (13) extending from opposing sides of the shaft (11) as is seen in both FIGS. 1 & 2. Electrode arm members (13) may be formed of an electrically conductive metal composition for transmission of electrical energy. Electrode arms (13) may be formed of any type of electrically conductive composition with the only exception being that such be expandable in the radial direction and provide sufficient structural integrity to support the forces applied thereto during expansion and during operation within the patient's body and further being biocompatible with respect to the patient's body. Such electrically conductive compositions are well known in the art and will not be further discussed.

As seen in FIGS. 1 and 2, each of the expandable electrodes 10 includes at least two arcuate arm members 13 extending transverse the longitudinal direction 12 from opposing sides of electrically conductive shaft 11. Electrically conductive arm members have overlapping sections (as shown in FIG. 1) prior to a radial expansion of the electrically conductive expandable electrodes 10. As further seen in FIGS. 1 and 2, arcuate arm members are disposed in a substantially singular plane each with respect to the other.

Electrically conductive arm members 13 may have embedded within or otherwise affixed thereto, piezoelectric elements 200. The piezoelectric effect is reversible so that materials or compositions may exhibit a direct piezoelectric effect which is the internal generation of electric charge resulting from an applied mechanical force, or alternatively, a reverse piezoelectric effect which is the internal generation of mechanical strain resulting from an electric field such as from electrical generator 51 embedded in electrically conductive shaft 11.

Piezoelectric elements 200 may be formed of well-known compositions which include barium titanate and lead zirconate titanate which exhibit larger displacements as induce larger electric voltages than that found in natural mono crystalline materials.

In this manner, lead system 106 both generates and senses electrical energy to and from mammalian tissue within a patient's body and/or the walls of the patient's vessel 20. Electrical generator 51 thus produces and senses electrical energy passing to and from the vessel 20.

In general, lead system (106) may be formed of a plurality of electrically conductive expandable electrodes (10) each displaced from the other by a predetermined distance as is clearly seen in FIGS. 1 & 2. Each of the electrically expandable electrodes 10 are electrically coupled to electrically conductive shaft 11.

Figure 4:
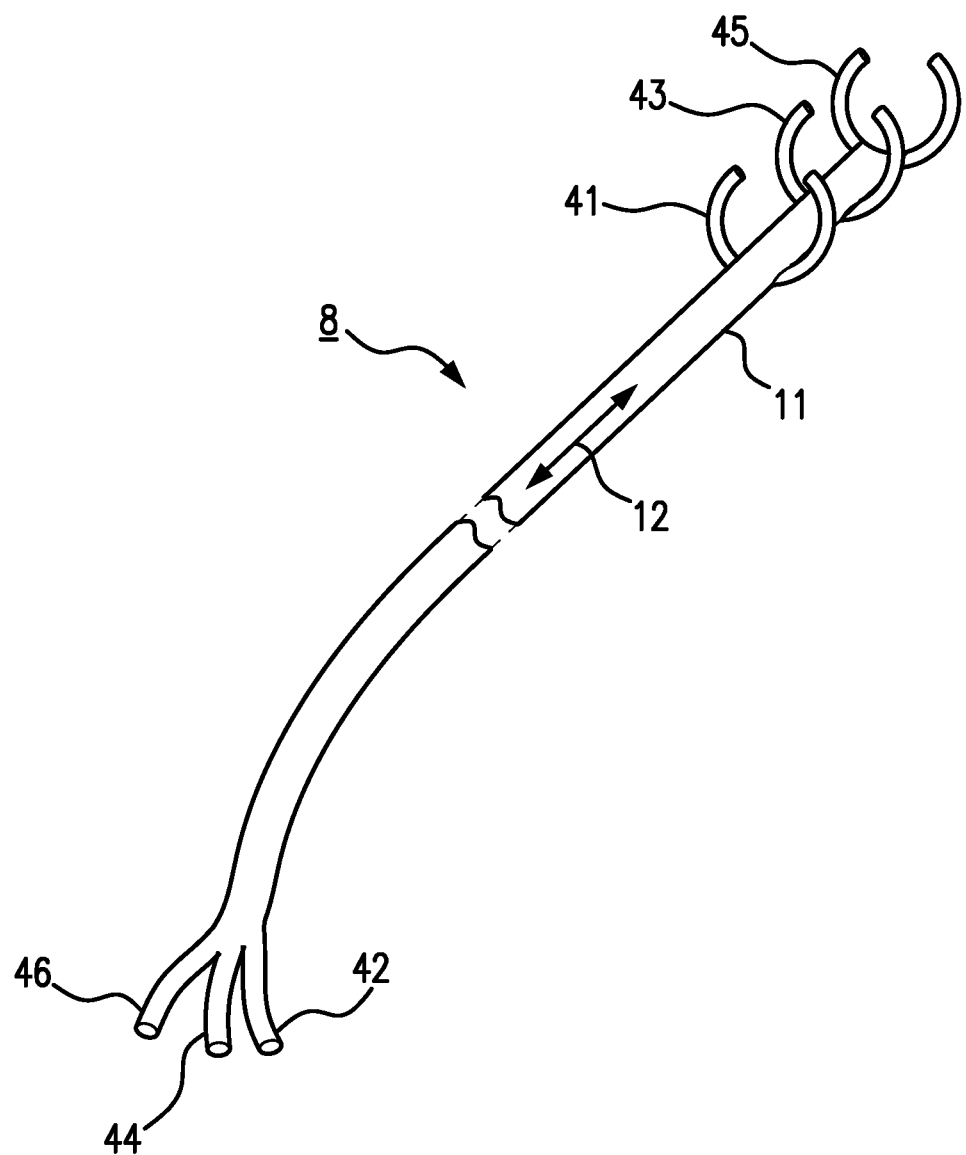
FIG. 4 is a schematic perspective view, partially cut away of the subject invention incorporated into a catheter structure.

A system (106) adaptable for pacemaking is shown in FIG. 4 having high voltage pacing electrodes (45) coupled to high voltage pacing port (46). Low voltage pacing electrodes (43) are coupled to lead (11) and the electrical energy is passed through low voltage pacing port (44). System (106) may include sensing electrodes (41) which are electrically coupled to sensing port (42).

In certain exemplary applications, ring-like electrodes (10) may be introduced percutaneously over a conventional balloon tipped catheter, or may be surgically implanted. Where a balloon tipped catheter is used, balloon inflation subsequent to introduction causes responsive expansion of the electrode rings so that they contact the lining of the cardiac chambers or vessel walls. The balloon (37) may then be deflated and the catheter extracted, leaving the electrodes (10) in contact with the vascular endothelium as shown in FIG. 2.

System (8) may include expansion mechanism (34) for radially displacing electrodes (10) into interfacing relationship with the inner wall of a patient's vessel (20). Expansion mechanism (34) may include a well-known balloon catheter which includes the balloon (37) for insert through the openings (108), shown in FIG. 1, and then expanded to deploy the expandable electrodes (10) into the deployed position as shown in FIG. 2. Balloon catheters are well-known in the prior art and have previously been used in particular for stent placement within a vessel. Once the balloon catheter has been inserted through the openings (108) through pressure differentials, expandable arm members (13) may be deployed.

Preferably, the ring electrodes (10) comprise ultrasound and electromagnetic receiver electrodes. Compared to prior art, the current invention provides such advantages as closer electrode contact with a larger surface area of tissue. With greater surface area of electrodes, less amount of energy is needed to stimulate tissue. Additionally, flat shaped electrodes may be provided (compared to the round cylindrical shaped conventional electrodes) for more effective endothelium coverage, minimizing the risk of clot formation or infection.

In accordance with one embodiment of the present invention, wireless piezoelectric elements are thereby implanted within the vascular or muscular structures of the vascular system. Their stimulation by external or implantable ultrasound and Doppler transmitter measures allow for transduced wireless stimulation of the tissues, when the piezoelectric elements convert their externally stimulated mechanical energy to electrical energy. A self-retaining wireless implantable electrode system 106 operable in this manner with piezoelectric elements 200 is heretofore unseen.

In certain alternate embodiments, the ring electrodes are attached to a power source to enable sensing, low voltage pacing and high voltage pacing.

Conventional pacemaker generators permit sensing of electrical cardiac action by use of electrodes imbedded into the endocardium or vascular structures of the heart. Without electrodes, generators are unable to detect electrical or mechanical cardiac action. For a wireless system, it would be desirable that generators serve both to detect and induce electrical and mechanical action. In addition, conventional generators are disc shaped and may not be suitable for use in close proximity to cardiac structures. A generator having curved and elongated shape would be more desirable to conform to the intercostals space (the space between the ribs of the chest overlying the heart), and permit sufficient proximity to cardiac structures for effective transfer of electrical, ultrasound, Doppler, infrared and magnetic signals.

Figure 8:
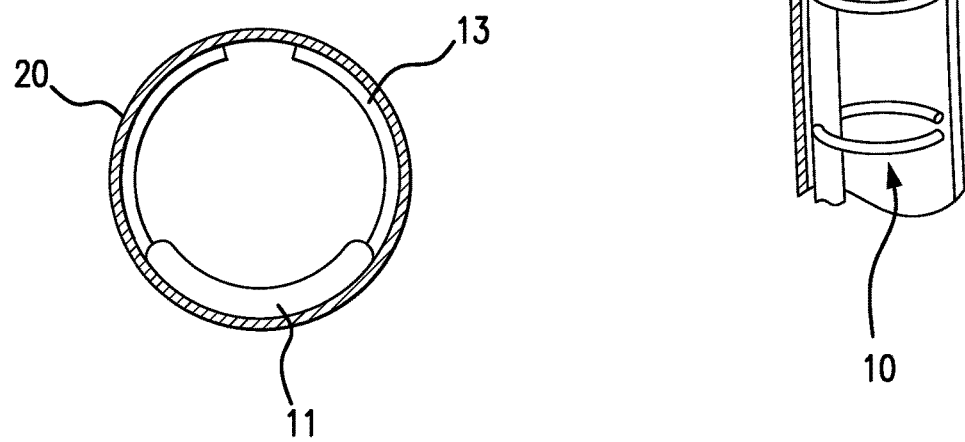

FIG. 1 shows an exemplary embodiment of a system formed in accordance with the present invention. The system includes a series of overlapping ring-shaped electrodes (10), as configured prior to deployment. For clearer illustration of its components, the system is shown separate from the balloon tipped catheter (illustrated in FIG. 3) which preferably carries the system's electrodes 10 to their deployment position. The ring electrodes (10) are attached to a shaft (11) that has a low or flat profile, and may have a curved profile as shown in FIG. 8 to conform to the inner surface contour 20, so as to minimally interfere with blood flow, and maintain contact with the lining of the surrounding tissues (such as blood vessels, or heart chambers). While electrodes (10) are shown having a circular cross-sectional shape in FIG. 1, such is provided for illustrative purposes only and may be configured to have alternative cross-sectional shapes, for example, rectangular, or oval cross-sectional contours.

FIG. 2 illustrates the ring electrodes (10) in their deployed configuration. They may be placed in such configuration by inflating the balloon catheter (FIG. 3), whereby the ring electrodes are expanded to closely conform to the shape of the vessel or chamber that needs to be stimulated. Contact with the lining of the vessel or chamber is essential for body fluids to flow freely and tissue to grow to cover the electrodes with endothelium (lining of the vessels), such that clot formation may be prevented. The ring electrodes (10) and shaft (11) are made of a material that is flexible, and which conducts electricity. Piezoelectric components 200 are incorporated with the electrodes (10), and/or with the shaft (11) of the electrodes.

Figure 3:
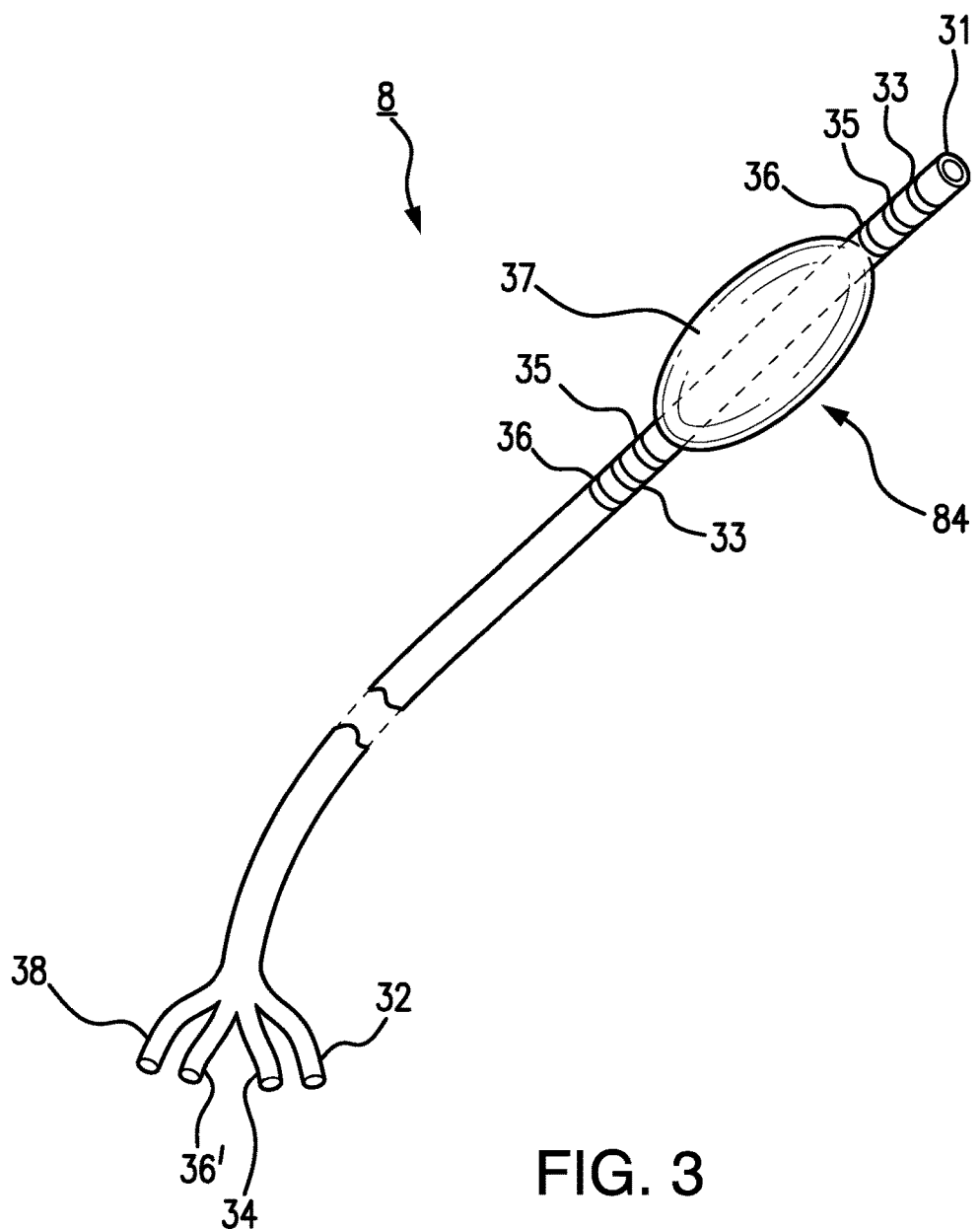
FIG. 3 is a schematic perspective view, partially cut away, illustrating a catheter usable to introduce the system of the present concept into a cardiac or intravascular structure of a patient.

FIG. 3 illustrates a balloon tipped multi-lumen catheter that may be used to carry the wireless ring electrodes to their destination. The catheter is equipped with flow meter, pressure manometer, and sensing and pacing electrodes to assist in proper positioning of the ring electrodes. The catheter is equipped with sensors to continuously monitors distal (31) and proximal (32) pressures, blood flow (33), and electrical thresholds (35), as well as with ultrasound imaging transducers (36). The balloon (37) is inflated and deflated from a proximal port (38).

Ring-like electrodes 10 may be introduced percutaneously over a conventional balloon tipped catheter or otherwise be surgically implanted. Balloon 37 inflation causes a responsive expansion of the electrode rings 10 in order that they are positioned contiguous to the lining of the cardiac chambers or walls of vessel 20. Subsequently, balloon 37 may be deflated and the catheter extracted with the electrodes 10 and arm members 13 in contact with the vascular endothelium as shown in FIG. 2. Ring electrodes 10 may include ultrasound and electromagnetic receiver electrodes contiguous to generator 51 embedded within the lead system 106.

Referring to FIG. 4, there is shown a representative multi-lumen catheter (40) provided with distal ring electrodes respectively for sensing (41), low voltage pacing (43), and high voltage pacing (45). The ring electrodes are coupled to corresponding proximal ports for, respectively, sensing (42), low voltage pacing (44) and high voltage pacing (46). Connections to an implantable generator are suitably made (not shown).

The catheter (40) is introduced over a temporary low profile balloon system (such as illustrated in FIG. 3) similar to that employed in prior catheters. Balloon inflation causes the distal ring electrodes to expand at the desired location in the given vascular system or heart chambers. Once the electrodes (10) are expanded to secure in place, the temporary balloon catheter is deflated and removed from the body, leaving the multi-lumen catheter in place.

Figure 5:
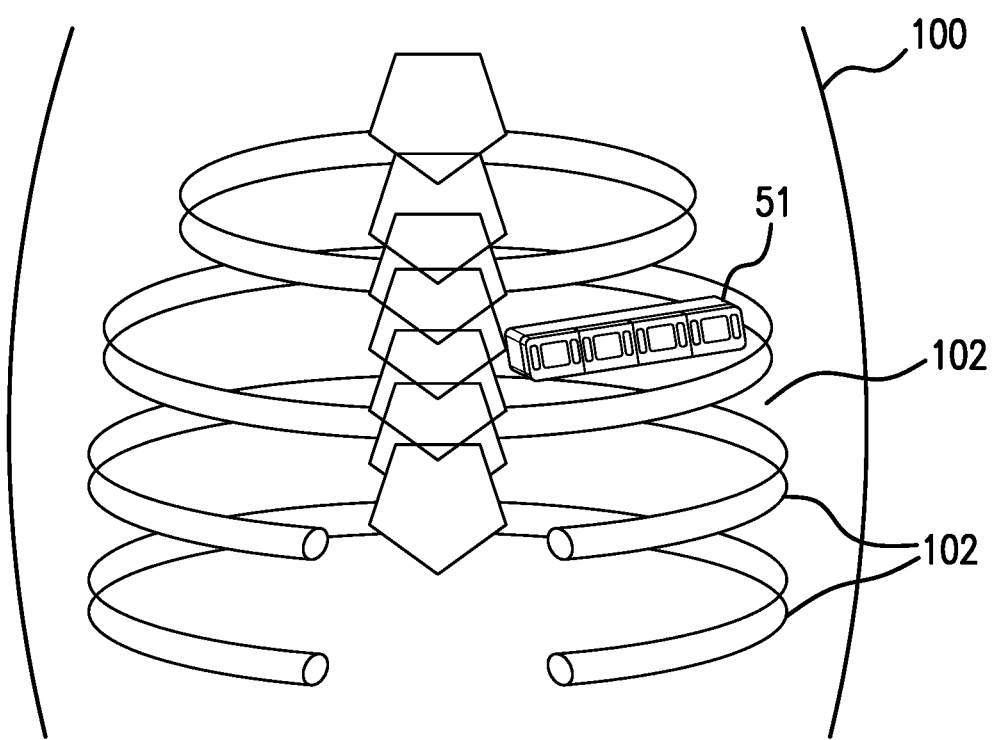
FIG. 5 is a schematic perspective view of an embodiment of the subject concept illustrating a generator system disposed in an intercostal space within the patient's anatomy.

FIG. 5 is a schematic diagram illustrating the inter-costal space (102), in close proximity with which expandable electrodes (10) of the present invention may have been deployed. An ideal location for a generator (51) would normally be free of intervening bone matter or lung tissue that might otherwise interfere with ultrasonic signals, which tend to transmit poorly through air present in lung tissue, and through bone matter.

Figure 6:
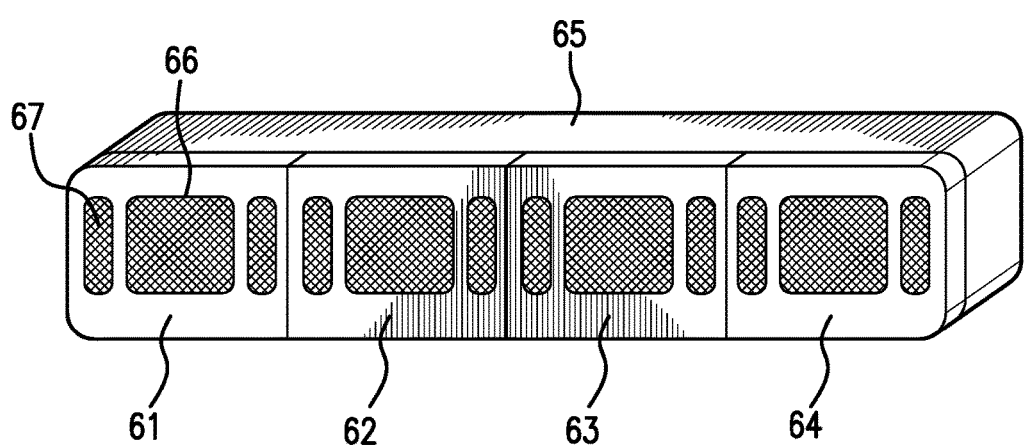
FIG. 6 is a schematic perspective view of an electrical generator which may be mounted within a patient's body.
Figure 7:
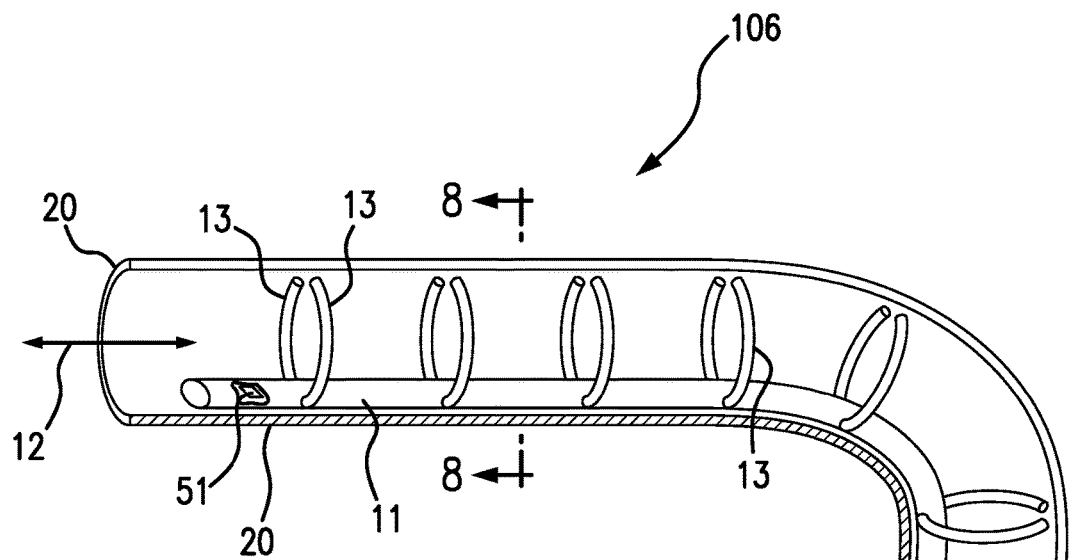
FIG. 7 is a schematic perspective view of the subject concept showing a flexible shaft of the subject concept within the vessel of a patient; and, FIG. 8 is a cross-section of the system shown in FIG. 7 taken along the Section Line 8-8.

FIG. 6 shows a generator (65) such as disposed in the inter-costal space of FIG. 5. The generator (65) comprises elements for ultrasonic pacing (61), ultrasonic and Doppler imaging (62), low voltage pacing (63), and high voltage pacing (64). The generator (65) is surgically fixed within the inter-costal space at an optimum location determined by the ultrasonic (66) (or echocardiographic) window. Such imaging elements are disposed to face the heart or the tissue to be stimulated. The generator (65) also comprises electrocardiographic electrodes (67) which may face the heart or the ribs, or may even face away from the heart, depending on the level of inter-costal muscle interference with the heart's electrical signals. Preferably, the power source is positioned behind or beside the pacing or imaging elements, so as not to interfere with their function. The power source may be of any suitable type commercially available, such as electrochemical or electromechanical.

The generator (65) may be flexible, curved, or made of movable pacing and imaging elements so as conform to the spaces between the ribs, and minimize unwanted cosmetic chest asymmetry. The advantages of the close proximity of echocardiographic and electrocardiographic electrodes near the tip of trans-esophageal probes has been previously shown (Combined Echo-electrocardiographic Probe, A-Hamid Hakki et al, U.S. Pat. No. 5,749,833).

According to one aspect of the present invention, a convenient and effective method of securely implanting a pacemaker lead into the vascular system (veins, arteries or lymphatic channels) of the heart is provided.

According to certain embodiments of the present invention, a multi-lumen catheter is introduced into the venous system of the heart, implanting electrodes at various locations within the cardiac veins for optimal pacing. The locations are determined by the resultant pacing induced electrical and mechanical efficiency. Conventional steering mechanisms are utilized for introducing pacemaker leads and maneuvering in different cardiac chambers and vessels. Steerable flexible wire systems may be introduced via the multi-lumen catheter.

According to yet other embodiments of the present invention, a multi-lumen catheter is introduced into the venous system of the heart, implanting electrodes at various locations within the cardiac veins for optimal pacing. The ring electrodes are bipolar with distal cathode and proximal anode.

According to still other embodiments of the present invention, a multi-lumen catheter is introduced into the venous system of the heart, implanting electrodes at various locations within the cardiac veins for optimal pacing. The electrodes are detachable and embedded in the lining of the vessel.

In other embodiments, a multi-lumen catheter is introduced into the venous system of the heart, implanting electrodes at various locations within the cardiac veins for optimal pacing. The electrodes are made of suitable material such as platinum, iridium that provides optimal sensing, pacing, and shock.

In certain other embodiments, the ring electrodes are equipped with receiver transducer circuitry any suitable type known in the art capable of converting ultrasound energy to electric energy to be transmitted to the electrodes.

In certain other embodiments, a multi-lumen catheter is introduced into the arterial system of the heart, implanting electrodes at various locations within the cardiac arterial system for optimal pacing. The ring electrodes are made of suitable material known in the art to be resistant to thrombus formation.

In certain other embodiments, the electrodes are coated with suitable material known in the art to be resistant to thrombus formation.

In certain other embodiments, the electrodes are formed of a suitable material known in the art having drug eluting properties.

In certain other embodiments, the electrodes are located in vascular beds of each of the four cardiac chambers in order to provide homogeneous electrical stimulation and defibrillation.

In certain other embodiments, the generator that energizes the leads is powered by a battery, and produces electrical stimulation.

In certain other embodiments, the generator that energizes the leads is powered by a stimulator that produces electrical current via body tissue without the need for a wire lead.

In certain other embodiments, the generator produces ultrasound energy that is transmitted to the electrodes equipped with receiver transducer circuitry operable to convert ultrasound energy to electric energy for transmission to the electrodes.

In certain other embodiments, the generator is curved and elongated in shape in order to conform to the intercostal space (the space between the ribs of the chest overlying the heart), and permit close proximity to cardiac structures for optimal transfer of electrical, ultrasound, Doppler, infrared and magnetic signals therewith.

In certain other embodiments, the generator is operable to detect cardiac electrical activity without the use of intracardiac electrodes.

In certain other embodiments, the generator is operable to emulate a 12-lead electrocardiogram by detecting cardiac electrical activity from various locations of the heart.

In certain other embodiments, the generator is operable to induce cardiac electrical signals without the use of electrodes.

In certain other embodiments, the generator is operable to detect cardiac mechanical activity by way of ultrasound or Doppler signals without the use of intracardiac electrodes.

In certain other embodiments, the generator is operable to induce cardiac mechanical contraction by way of ultrasound signals without the use of wire electrodes.

In certain other embodiments, the generator is operable to receive cardiac electrical and mechanical action and synchronize the output signals to electrodes implanted in various cardiac chambers in order to provide optimal cardiac contraction and function.

What is claimed is:

1. A system for generating and sensing electrical energy to and from tissue within a mammalian body comprising:
   a flexible shaft insertable within the mammalian body, said shaft having a shaft axis line;
   an electrical generator embedded within the flexible shaft for producing and sensing electrical energy; and,
   at least one electrically conductive expandable electrode coupled to said electrically conductive shaft, said expandable electrode being radially displaceable with respect to said shaft axis line defining a longitudinal direction for contiguous contact with a wall of said tissue, said expandable electrode including at least two arcuate arm members extending transverse said longitudinal direction from opposing sides of said flexible shaft and having overlapping sections prior to said radial expansion of said at least one electrically conductive expandable electrode, said at least two arcuate arm members disposed in a substantially singular plane each with respect to the other, said at least two arm members being displaceable responsive to activation by said electrical generator.

2. The system as recited in claim 1 including a balloon catheter for insert within an opening formed by said at least one electrically conductive expandable electrode having an arcuate contour forming said opening whereby said balloon catheter contacts an inner periphery of said at least one electrically conductive expandable electrode and radially displaces said at least one electrically conductive electrode upon inflation of a balloon positioned on said balloon catheter.

3. The system as recited in claim 1 including a plurality of electrically conductive electrodes mounted to said flexible shaft, each of said electrically conductive expandable electrodes being displaced each from the other by a predetermined distance along said shaft axis line.

4. The system as recited in claim 1 where each of said two arcuate arm members are rectangularly contoured in circumferential cross-section.

5. The system as recited in claim 1 where each of said two arcuate arm members are circularly contoured in circumferential cross-section.

6. The system as recited in claim 1, where said flexible shaft is adapted to be inserted within a patient's vessel.

7. The system as recited in claim 1 where said at least one electrically conductive expandable electrode is selected from the group consisting of high voltage pacing electrodes, low voltage pacing electrodes and parameter sensing electrodes.

8. The system as recited in claim 7 where said electrical generator embedded within said flexible shaft detects mammalian body electrical activity and mechanical activity from said parameter sensing electrode.

9. The system as recited in claim 7 where said electrical generator embedded within said flexible shaft generates electrical energy to said high voltage pacing electrodes and said low voltage pacing electrodes.

10. The system as recited in claim 1 where each of said two arcuate arm members have embedded therein elements having a piezoelectric composition.

11. The system as recited in claim 1 where each of said two arcuate arm members are formed at least partially of a piezoelectric composition.

12. The system as recited in claim 1 where each of said two arcuate arm members include a circumferential cross-sectional shape selected from the group of a rectangular contour, a circular contour, an oval contour and a polygonal contour.

13. The system as recited in claim 1 where said embedded electrical generator includes an ultrasound and Doppler source for pacing in proximity to said electrically conductive electrode.

14. The system as recited in claim 1 including an expansion mechanism adjacent to said flexible shaft adapted to radially expand said arcuate arm members into interfering relationship with mammalian body tissue.

15. The system as recited in claim 1 including an expansion mechanism positioned within said flexible shaft adapted to radially expand said arcuate arm members into interfering relationship with mammalian body tissue.

16. The system as recited in claim 1 where said electrical generator embedded within said flexible shaft is electrically and wirelessly coupled to said at least one electrically conductive expandable electrode.

17. The system as recited in claim 1 wherein said flexible shaft is formed of an electrically conductive composition for electrical communication with said at least two arcuate arm members.

18. The system as recited in claim 1 where said flexible shaft is formed of a non-electrically conductive composition.

19. The system as recited in claim 1 wherein said flexible shaft taken in cross-section to said shaft axis line is contoured to assume a shape of a mammalian vessel.

\* \* \* \* \*